United States Patent
Gunji et al.

(10) Patent No.: US 7,169,587 B2
(45) Date of Patent: Jan. 30, 2007

(54) METHOD FOR PRODUCING L-LYSINE OR L-ARGININE BY USING METHANOL ASSIMILATING BACTERIUM

(75) Inventors: Yoshiya Gunji, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/166,142

(22) Filed: Jun. 11, 2002

(65) Prior Publication Data

US 2003/0124687 A1 Jul. 3, 2003

(30) Foreign Application Priority Data

Jun. 12, 2001 (JP) .............................. 2001-177075

(51) Int. Cl.
C12P 13/08 (2006.01)
C12N 1/20 (2006.01)
C12N 15/00 (2006.01)
C07K 1/00 (2006.01)
C07H 21/02 (2006.01)

(52) U.S. Cl. .............. 435/115; 435/252.3; 435/252.33; 435/320.1; 530/350; 536/23.1

(58) Field of Classification Search ................ 435/115, 435/252.3, 252.33, 320.1; 530/350; 536/23.1
See application file for complete search history.

(56) References Cited

U.S. PATENT DOCUMENTS 5,643,758 A * 7/1997 Guan et al. ................ 435/69.7
5,972,663 A 10/1999 Winterhalter et al.
6,303,381 B1 10/2001 Gunji et al.

FOREIGN PATENT DOCUMENTS

AU 199719218 B2 9/1997
EP 1 016 710 A2 7/2000
WO WO97/23597 7/1997

OTHER PUBLICATIONS

Attwood et al. Which craft is best in bioinformatics? Comput. Chem. 2001, vol. 25(4), pp. 329-339.*
Ponting, C.P. Issues in predicting protein function from sequence. Brief. Bioinform. Mar. 2001, vol. 2(1), pp. 19-29.*
Accession X96471. Mar. 19, 2001.*
Roche et al. Microbioloy. Oct. 1997;143 ( Pt 10): 3309-12.*
Vrljic et al. Journal of Molecular Microbiology and Biotechnology (1999), 1(2), 327-336.*
Balbas et al. Gene. Jun. 12, 1996;172(1):65-9.*
Marina Vrljic, et al., "A new type of transporter with a new type of cellular function: L-lysine export from *Corynebacterium glutamicum*", Molecular Microbiology (1996) 22(5), pp. 815-826.
EPO Search Report, Dec. 12, 2003.
Vrljic et al. "A new type of transporter with a new type of cellular function: L-lysine export from *Corynebacterium glutamicum*" Molecular Microbiol. 22(5):815-826 (1996).
Motoyama et al. "Characterization of the Asparate Family Amino Acids Biosynthetic Enzymes in L-Threonine- and L-Lysine-producing Mutants of *Methylobacillus glycogenes*" Biosci. Biotech. Biochem. 57(3):461-466 (1993).
Motoyama et al. "Amino Acid Production from Methanol by *Methylobacillus glycogenes* Mutants: Isolation of L-Glutamic Acid Hyper-producing Mutants from *M. glycogenes* Strains, and Derivation of L-Threonine and L-Lysine-producing Mutants from Them" Biosci. Biotech. Biochem. 57(1):82-87 (1993).
Lee et al. "Lysine Production from Methanol at 50° C. Using *Bacillus methanolicus*: Modeling Volume Control, Lysine Concentration, and Productivity Using a Three-Phase Continuous Simulation" Biotech. Bioengin. 49:639-653 (1996).
Schendel et al. "L-Lysine Production at 50° C. by Mutants of a Newly Isolated and Characterized Methylotrophic *Bacillus* sp." Applied and Environ. Microbiol. 56(4):963-970 (1990).
Motoyama et al. "Overproduction of L-Lysine from Methanol by *Methylobacillus glycogenes* Derivatives Carrying a Plasmid with a Mutated dapA Gene" Applied and Environ. Microbiol. 67(7):3064-3070 (2001).
Bellman et al. "Expression control and specificity of the basic amino acid exporter LysE of *Corynebacterium glutamicum*" Microbiology 147:1765-1774 (2001).
Presentation slides and speech by Yoshiya Gunji at the Annual Meeting of the Society for Biotechnology, Japan held at Meijyou University on Sep. 23, 2004.

* cited by examiner

Primary Examiner—Tekchand Saidha
Assistant Examiner—Christian L. Fronda
(74) Attorney, Agent, or Firm—Cermak & Kenealy, LLP; Shelly Guest Cermak

(57) ABSTRACT

A DNA encoding a variant of a protein, having a loop region and six hydrophobic helixes and involved in excretion of L-lysine to outside of a cell, wherein the DNA encodes a mutant protein not containing the loop region that is contained in a wild-type protein and facilitates excretion of L-lysine, L-arginine or both of these L-amino acids to outside of a cell of a methanol assimilating bacterium when the DNA is introduced into the bacterium, specifically lysE24, is introduced into a methanol assimilating bacterium such as *Methylophilus* bacteria to improve L-amino acid productivity, especially L-lysine and L-arginine productivities.

19 Claims, 2 Drawing Sheets

METHOD FOR PRODUCING L-LYSINE OR L-ARGININE BY USING METHANOL ASSIMILATING BACTERIUM

BACKGROUND OF THE INVENTION

1. Field of the Invention

The present invention relates to techniques used in the field of microbial industry. More precisely, the present invention relates to a method for producing L-lysine or L-arginine by fermentation and a microorganism used in the production method.

2. Description of the Related Art

Amino acids such as L-lysine, L-glutamic acid, L-threonine, L-leucine, L-isoleucine, L-valine and L-phenylalanine are industrially produced by fermentation using microorganisms that belong to the genus *Brevibacterium, Corynebacterium, Bacillus, Escherichia, Streptomyces, Pseudomonas, Arthrobacter, Serratia, Penicillium, Candida* or the like. In order to improve the productivity of these microorganisms, strains isolated from nature or artificial mutants thereof have been used. Moreover, various techniques have been disclosed for increasing the L-amino acid producing abilities by using recombinant DNA techniques to enhance L-amino acid biosynthetic enzymes.

Productivities of L-amino acids have been considerably increased by breeding of microorganisms such as those mentioned above and improvements of production methods. However, in order to respond to further increase in demands in future, development of methods for more efficiently producing L-amino acids at lower cost have still been desired.

As methods for producing L-amino acids by fermentation of methanol, which is a fermentation raw material available in a large amount at a low cost, there have hitherto known methods using microorganisms that belong to the genus *Achromobacter* or *Pseudomonas* (Japanese Patent Laid-open (Kokai) No. 45-25273), *Protaminobacter* (Japanese Patent Publication (Kokoku) No. 49-125590), *Protaminobacter* or *Methanomonas* (Japanese Patent Laid-open No. 50-25790), *Microcyclus* (Japanese Patent Laid-open No. 52-18886), *Methylobacillus* (Japanese Patent Laid-open No. 4-91793), *Bacillus* (Japanese Patent Laid-open No. 3-505284) and so forth. The inventors of the present invention have so far developed methods for producing L-amino acids using *Methylophilus* bacteria based on breeding by artificial mutagenesis and recombinant DNA techniques (Japanese Patent Application No. 11-368097).

In recent years, there have been identified proteins that have a function of specifically excreting an L-amino acid to outside a cell of microorganism and genes therefor, and in particular, Vrljic et al. identified a gene involved in excretion of L-lysine from a *Corynebacterium* bacterium to outside of a cell (Vrljic M., Sahm H., Eggeling L., Molecular Microbiology 22:815–826 (1996)). This gene was designated as lysE, and it was reported that L-lysine producing ability of *Corynebacterium* bacteria could be improved by enhancing this gene in *Corynebacterium* bacteria (WO97/23597). It is also known that productivities for some L-amino acids can be improved by increasing expression amounts of amino acid excreting proteins in *Escherichia coli* (Japanese Patent Laid-open No. 2000-189180). For example, it is reported that productivities of cysteine, cysteine and so forth can be improved by enhancing expression of ORF306 gene in *Escherichia coli* (EP885962).

However, there has so far been disclosed no example of demonstrating that the excretion process of an amino acid constitutes a serious obstacle for amino acid production by fermentation of methanol using a methanol assimilating bacterium. There is also no report on any amino acid excretion gene that can provide such an excretion activity in a methanol assimilating bacterium.

Furthermore, it has not been known that the lysE gene has a function of excreting amino acids other than L-lysine.

SUMMARY OF THE INVENTION

An object of the present invention is to provide a method for efficiently producing L-lysine or L-arginine by using methanol, which is available in a large amount at a low cost.

The inventors of the present invention assiduously studied in order to achieve the aforementioned object. As a result, they found that, when an L-amino acid is produced by utilizing a methanol assimilating bacterium, especially a *Methylophilus* bacterium, the excretion process of the L-amino acid to outside of cells constituted one of barriers. Further, they successfully isolated a gene that could provide excretion activity of the amino acid, especially in the microorganism, as a factor for overcoming the barrier, and found that use of the gene enabled efficient amino acid production.

The inventors of the present invention introduced the already known lysE gene derived from a *Corynebacterium* bacterium into a methanol assimilating bacterium and investigated its effect on the amino acid production. However, a mutation or deletion was caused in the introduced lysE gene and thus lysE could not be functioned. Since a protein responsible for such excretion exerts its function when it is incorporated into a cytoplasmic membrane, there must be suitable relationships between the protein and properties of the membrane such as its lipid composition. Therefore, it is considered difficult to obtain expression of a membrane protein of heterogenous origin in a form that exerts its function, and the above results supported it.

The inventors of the present invention obtained by chance a mutant gene that could function in a methanol assimilating bacterium during study of the aforementioned genes for excretion of L-amino acids. They also found a remarkable effect of utilization of the mutant gene in amino acid production using a methanol assimilating bacterium.

The present invention was accomplished as described above and provides the followings.

(1) A DNA encoding a variant of a protein, the protein having a loop region and six hydrophobic helixes and involved in excretion of L-lysine to outside of a cell, wherein the DNA encodes a mutant protein not containing the loop region that is contained in a wild-type protein and facilitates excretion of L-lysine, L-arginine or both of these L-amino acids to outside of a cell of a methanol assimilating bacterium when the DNA is introduced into the bacterium (2) The DNA according to (1), wherein the mutant protein substantially consists only of the hydrophobic helixes.

(3) The DNA according to (1) or (2), wherein the mutant protein has all of the six hydrophobic helixes.

(4) The DNA according to any one of (1) to (3), which encodes a peptide containing the first to third hydrophobic helixes from the N-terminus and a peptide containing the fourth to sixth hydrophobic helixes from the N-terminus.

(5) The DNA according to any one of (1) to (4), wherein the protein is LysE protein.

(6) The DNA according to (5), wherein the LysE protein is LysE protein of a coryneform bacterium.

(7) The DNA according to any one of (1) to (5), wherein the methanol assimilating bacterium is a *Methylophilus* bacterium.

(8) A DNA encoding a protein selected from the following proteins:

(A) a protein which comprises the amino acid sequence of SEQ ID NO: 10, and (B) a protein which comprises the amino acid sequence consisting of the amino acid sequence of SEQ ID NO: 10 including substitution, deletion, insertion or addition of one or several amino acid residues and shows an activity for facilitating excretion of L-lysine, L-arginine or both of these L-amino acids to outside of a cell of a methanol assimilating bacterium.

(9) A *Methylophilus* bacterium, into which the DNA according to any one of (1) to (8) is introduced in an expressible form and has an ability to produce L-lysine or L-arginine.

(10) A method for producing L-lysine or L-arginine, comprising culturing the *Methylophilus* bacterium according to (9) in a medium to produce and accumulate L-lysine or L-arginine in culture and collecting the L-lysine or L-arginine from the culture.

(11) The method for producing L-lysine or L-arginine according to (10), wherein the medium contains methanol as a main carbon source.

In the present invention, the expression of "facilitating excretion of L-lysine, L-arginine or both of these L-amino acids to outside of a cell" means that, when a methanol assimilating bacterium containing the DNA of the present invention is cultured in a medium, it provides an increased amount of L-lysine, L-arginine or both of these L-amino acids excreted into the medium compared with the methanol assimilating bacterium not containing the DNA of the present invention. The promotion of excretion of the L-amino acids from the inside of the cell to the outside of the cell is observed as increased concentrations of the L-amino acids accumulated in the medium during the culture of the methanol assimilating bacterium containing the DNA of the present invention compared with the concentrations provided by the methanol assimilating bacterium not containing the DNA of the present invention, which increased concentrations are provided as a result of the promotion. Further, the promotion of excretion of the L-amino acids to outside of a cell may be also observed as decrease of intracellular concentrations of the L-amino acids when the DNA of the present invention is introduced into a methanol assimilating bacterium.

According to the present invention, L-amino acid productivity, especially L-lysine and L-arginine productivity, of a methanol assimilating bacterium can be improved.

PREFERRED EMBODIMENTS OF THE INVENTION

Figure 1:
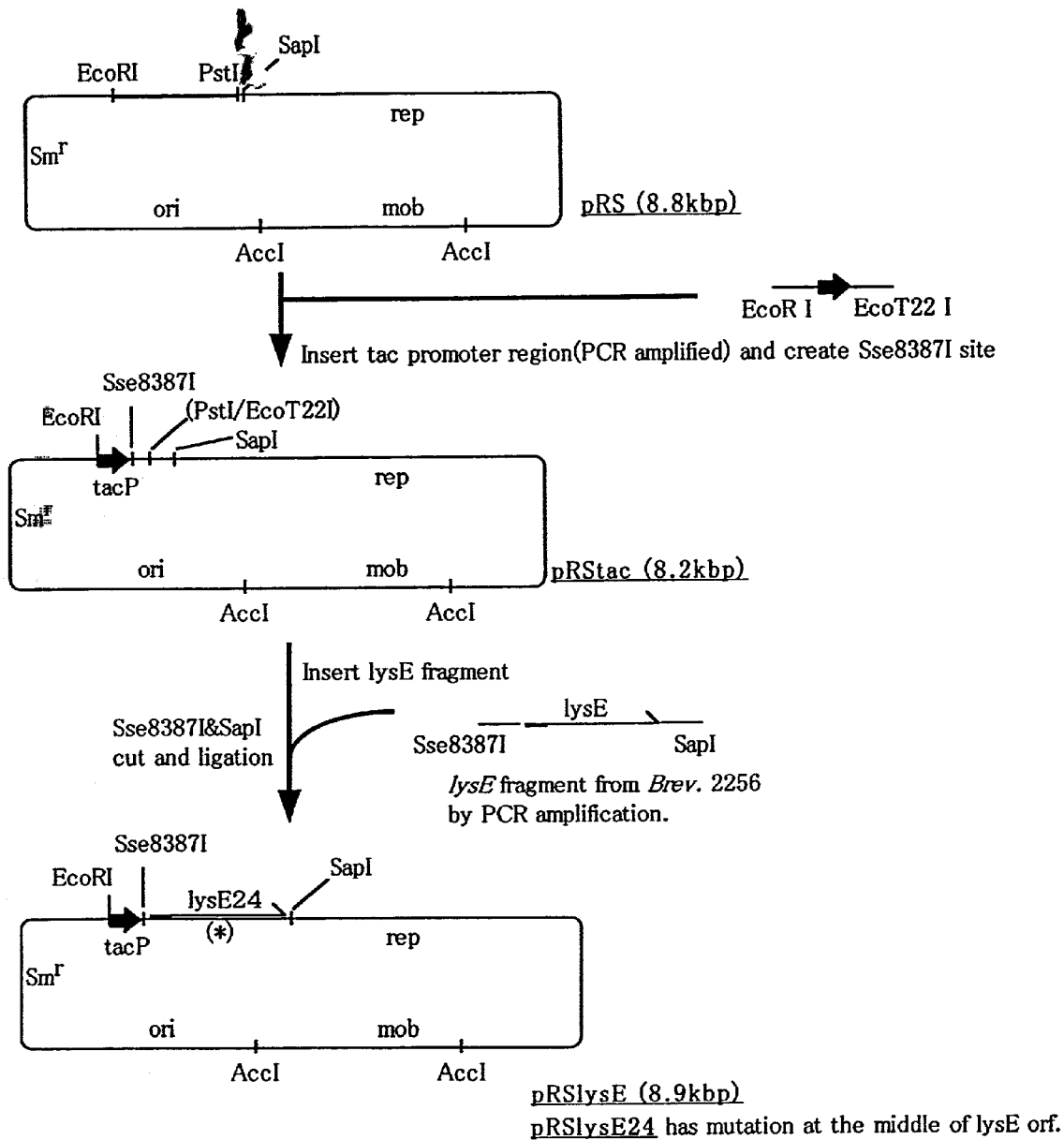
FIG. 1 shows constructions of a plasmid pRStac having the tac promoter and plasmids pRSlysE and pRSlysE24 consisting of the plasmid pRStac inserted with the lysE gene or lysE24 gene.

Hereafter, the present invention will be explained in detail.

<1> DNA of the Present Invention

The DNA of the present invention is a DNA that promotes excretion of L-lysine, L-arginine or both of these L-amino acids to outside of a cell when it is introduced into a methanol assimilating bacterium, and it is a DNA that encodes a variant of a protein involved in the excretion of L-lysine to outside of a cell of the microorganism.

In the present invention, the methanol assimilating bacterium is a bacterium that can grow by using methanol as a main carbon source, and it is a bacterium of which excretion of L-amino acids such as L-lysine or L-arginine to the outside of the cell is enhanced by introducing the DNA of the present invention into it. Specifically, *Methylophilus* bacteria such as *Methylophilus methylotrophus* can be mentioned. Examples of *Methylophilus methylotrophus* include the AS1 strain (NCIMB10515) and so forth. The *Methylophilus methylotrophus* ASI strain (NCIMB10515) can be obtained from the National Collections of Industrial and Marine Bacteria (Address: NCIMB Lts., Torry Research Station 135, Abbey Road, Aberdeen AB98DG, United Kingdom).

The DNA of the present invention can be obtained by introducing a mutation into a DNA encoding a protein having a loop region and six hydrophobic helixes and involved in excretion of L-lysine to outside of a cell to modify it so that the protein should not have the loop region or the protein should substantially consist only of the hydrophobic helixes. The expression of "substantially consisting only of the hydrophobic helixes" means that the mutant LysE is completely deficient in the loop region or deficient in most of the loop region to such an extent that the function of the mutant LysE should not be affected.

One of the embodiments of the DNA of the present invention is the DNA designated as lysE24, which will be described in the examples mentioned later. lysE24 is a mutant gene isolated from *Brevibacterium lactofermentum* as a homologue of the lysE gene reported for *Corynebacterium* bacteria. Therefore, the DNA of the present invention may also be referred to as a "mutant lysE" for convenience.

The LysE protein that is encoded by the lysE gene has six hydrophobic helix regions. Some of these hydrophobic regions are estimated to be transmembrane domains. It is also estimated that a region between the third and fourth regions from the N-terminus is hydrophilic and has a loop structure. In the present invention, this hydrophilic region is called a loop region. The nucleotide sequence of wild-type lysE and the amino acid sequence of the LysE protein of *Brevibacterium lactofermentum* are shown in SEQ ID NOS: 7 and 8. In this amino acid sequence, hydrophobic helix regions correspond to the amino acid numbers 5–20, 37–58, 67–93, 146–168, 181–203 and 211–232. The loop region corresponds to the amino acid numbers 94–145.

The inventors of the present invention found that the lysE gene exerted lethal action in a methanol assimilating bacterium, but a DNA encoding a variant of the LysE protein that did not have the loop region or substantially consisted only of the hydrophobic helixes promoted the excretion of L-lysine and/or L-arginine to outside of a cell of methanol assimilating bacterium. The DNA of the present invention encodes such a mutant LysE protein that does not have such the loop region that is contained in a wild-type LysE protein or a mutant LysE protein that substantially consists only of the hydrophobic helixes.

The aforementioned mutant lysE is not particularly limited so long as it has one or more hydrophobic helixes and promotes excretion of L-lysine, L-arginine or both of these L-amino acids when it is introduces into a methanol assimilating bacterium. Specifically, there can be mentioned a DNA encoding a mutant LysE that has all of the first to sixth hydrophobic helixes from the N-terminus. More specifically, there can be mentioned a DNA encoding a peptide containing the first to third hydrophobic helixes from the N-terminus and a peptide containing the fourth to sixth hydrophobic helixes from the N-terminus. The aforementioned lysE24 is an example of the mutant lysE that encodes a peptide containing the first to third hydrophobic helixes and a peptide containing the fourth to sixth hydrophobic helixes. The lysE24 gene is introduced by a mutation with a stop codon downstream from the region encoding the third hydrophobic helix. When a region downstream from this stop codon was deleted as described in the examples mentioned later, the *Methylophilus methylotrophus* AS1 strain to which such a lysE24 gene is introduced did not accumulate L-lysine in the medium. From this, it is estimated that a peptide containing the first to third hydrophobic helixes and a peptide containing the fourth to sixth hydrophobic helixes are separately translated and function in *Methylophilus methylotrophus*. In any case, if the lysE24 gene is introduced into a *Methylophilus* bacterium, the production amount of L-lysine or L-arginine will be improved.

As the microorganism that is used as an origin of such a DNA encoding a protein involved in excretion of L-lysine to outside of a cell, i.e., the lysE gene or its homologous gene, any microorganisms can be utilized so long as they have variants of the genes that can express the L-lysine excretion activity in a methanol assimilating bacterium. Specifically, there can be mentioned coryneform bacteria such as *Corynebacterium glutamicum* and *Brevibacterium lactofermentum*, *Escherichia* bacteria such as *Escherichia coli*, *Pseudomonas* bacteria such as *Pseudomonas aeruginosa*, *Mycobacterium* bacteria such as *Mycobacterium tuberculosis* and so forth.

When the amino acid excretion gene is enhanced in a *Methylophilus* bacterium, a recombinant DNA can be prepared by ligating its gene fragment to a vector functioning in the *Methylophilus* bacterium, preferably a multi-copy type vector, and introduced into the *Methylophilus* bacterium as a host to transform it. Alternatively, the gene can be incorporated into a transposon and introduced into chromosome. Further, it is also possible to ligate a promoter that induces strong transcription in a *Methylophilus* bacterium upstream from the gene.

The reference that discloses lysE (WO97/23597) shows only the case where the lysE gene of coryneform bacterium was introduced into a coryneform bacterium. And it mentions only L-lysine as the excreted amino acid and discloses a structure of the protein containing six transmembrane helixes as a novel protein excretion system including LysE. However, the inventors of the present invention confirmed that LysE derived from coryneform bacteria did not function at all in methanol assimilating bacteria. Furthermore, the factor that could be obtained is a factor of novel type that exert the excretion activity, which has a basic structure different from that of LysE of coryneform bacteria in which the six transmembrane helixes are constituted by one polypeptide, and this factor can no way be anticipated from the disclosure of the aforementioned patent specification that discloses lysE.

<2> *Methylophilus* Bacterium of the Present Invention

The *Methylophilus* bacterium of the present invention is a *Methylophilus* bacterium that is introduced with the DNA of the present invention in an expressible form and has an ability to produce L-lysine or L-arginine. It can be obtained by introducing the DNA of the present invention into a *Methylophilus* bacterium that has the L-lysine or L-arginine producing ability. The *Methylophilus* bacterium of the present invention can also be obtained by imparting an L-lysine or L-arginine producing ability to a *Methylophilus* bacterium introduced with the DNA of the present invention. The the *Methylophilus* bacterium of the present invention may also be one that has been imparted with an L-lysine or L-arginine producing ability by introduction of the DNA of the present invention in an expressible form.

A *Methylophilus* bacterium having the L-lysine or L-arginine producing ability can be obtained by imparting an L-lysine or L-arginine producing ability to a wild strain of a *Methylophilus* bacterium. In order to impart the L-lysine or L-arginine producing ability, there can be used methods conventionally used for breeding of coryneform bacteria, *Escherichia* bacteria and so forth, for example, acquisition of auxotrophic mutant strains, analogue resistant strains or metabolic regulation mutant strains, creation of recombinant strains in which an L-lysine or L-arginine biosynthesis system enzyme is enhanced (refer to "Amino Acid Fermentation", the Japan Scientific Societies Press [Gakkai Shuppan Center], 1st Edition, published on May 30, 1986, pp.77 to 100) and so forth. In the breeding of L-lysine or L-arginine producing bacteria, properties of auxotrophy, analogue resistance, metabolic regulation mutation and so forth may be individually imparted or two or more of them may be imparted in combination. The biosynthesis system enzyme may be individually enhanced or two or more of them may be enhanced in combination. Furthermore, the impartation of the properties including auxotrophy, analogue resistance, metabolic regulation mutation and so forth may be combined with the enhancement of biosynthesis system enzyme.

For example, L-lysine producing bacteria can be bred as mutant strains exhibiting auxotrophy for L-homoserine or L-threonine and L-methionine (Japanese Patent Publication Nos. 48-28078 and 56-6499), mutant strains exhibiting auxotrophy for inositol or acetic acid (Japanese Patent Laid-open Nos. 55-9784 and 56-8692), or mutant strains that are resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid or N-lauroylleucine.

Further, L-arginine producing bacteria can be bred as mutant strains resistant to a certain agent, for example, sulfa drug, 2-thiazolealanine, α-amino-β-hydroxyvaleric acid or the like; mutant strains exhibiting auxotrophy for L-histidine, L-proline, L-threonine, L-isoleucine, L-methionine or L-tryptophan in addition to resistance to 2-thiazolealanine (Japanese Patent Laid-open No. 54-44096); mutant strains resistant to ketomalonic acid, fluoromalonic acid or monofluoroacetic acid (Japanese Patent Laid-open No. 57-18989); mutant strains resistant to argininol (Japanese Patent Laid-open No. 62-24075); mutant strains resistant to X-guanidine (X represents a derivative of fatty acid or aliphatic chain, Japanese Patent Laid-open No. 2-186995); mutant strains resistant to 5-azauracil, 6-azauracil, 2-thiouracil, 5-fluorouracil, 5-bromouracil, 5-azacytosine, 6-azacytosine and so forth; mutant strains resistant to arginine hydroxamate and 2-thiouracil; mutant strains resistant to arginine hydroxamate and 6-azauracil (refer to Japanese Patent Laid-open No. 57-150381); mutant strains resistant to a histidine analogue or tryptophan analogue (refer to Japanese Patent Laid-open No. 52-114092); mutant strains exhibiting auxotrophy for at least one of methionine, histidine, threonine, proline, isoleucine, lysine, adenine, guanine and uracil (or uracil precursor) (refer to Japanese Patent Laid-open No. 52-99289); mutant strains resistant to arginine hydroxamate (refer to Japanese Patent Publication No. 51-6754); mutant strains exhibiting succinic acid auxotrophy or resistance to a nucleic acid base analogue (Japanese Patent Laid-open No. 58-9692); mutant strains deficient in ability to metabolize arginine and exhibiting resistance to an arginine antagonist and canavanine and auxotorophy for lysine (refer to Japanese Patent Laid-open No. 52-8729); mutant strains resistant to arginine, arginine hydroxamate, homoarginine, D-arginine and canavanine, or resistant to arginine hydroxamate and 6-azauracil (refer to Japanese Patent Laid-open No. 53-143288); mutant strains resistant to canavanine (refer to Japanese Patent Laid-open No. 53-3586) and so forth.

Hereafter, methods for imparting or enhancing L-amino acid producing ability by enhancing an L-amino acid biosynthetic enzyme gene will be exemplified below.

L-lysine producing ability can be imparted by, for example, enhancing activities of dihydrodipicolinate synthase and aspartokinase.

Activities of dihydrodipicolinate synthase and aspartokinase in a *Methylophilus* bacterium can be enhanced by transforming the *Methylophilus* bacterium host through introduction of a recombinant DNA prepared by ligating a gene fragment encoding dihydrodipicolinate synthase and a gene fragment encoding aspartokinase with a vector that functions in the *Methylophilus* bacterium, preferably a multiple copy type vector. As a result of the increase in the copy numbers of the gene encoding dihydrodipicolinate synthase and the gene encoding aspartokinase in cells of the transformant strain, activities of these enzymes are enhanced. Hereafter, dihydrodipicolinate synthase, aspartokinase and aspartokinase III are also referred with abbreviations of DDPS, AK and AKIII, respectively.

As a microorganism providing a gene that encodes DDPS and a gene that encodes AK, any microorganisms can be used so long as they can express DDPS activity and AK activity in a microorganism belonging to the genus *Methylophilus*. Such microorganisms may be wild strains or mutant strains derived therefrom. Specifically, examples of such microorganisms include *E. coli* (*Escherichia coli*) K-12 strain, *Methylophillus methylotrophus* AS1 strain (NCIMB10515) and so forth. Since nucleotide sequences have been revealed for a gene encoding DDPS (dapA, Richaud, F. et al., J. Bacteriol., 297 (1986)) and a gene encoding AKIII (lysC, Cassan, M., Parsot, C., Cohen, G. N. and Patte, J. C., J. Biol. Chem., 261, 1052 (1986)), these genes can be obtained by PCR using primers synthesized based on the nucleotide sequences of these genes and chromosomal DNA of microorganism such as *E. coli* K-12 as a template. As specific examples, dapA and lysC derived from *E. coli* will be explained below. However, genes used for the present invention are not limited to them.

It is preferred that DDPS and AK used for the present invention should not suffer feedback inhibition by L-lysine. It is known that wild-type DDPS derived from *E. coli* suffers feedback inhibition by L-lysine, and that wild-type AKIII derived from *E. coli* suffers suppression and feedback inhibition by L-lysine. Therefore, dapA and lysC to be introduced into a *Methylophilus* bacterium preferably encode for DDPS and AKIII having a mutation that eliminates the feedback inhibition by L-lysine, respectively. Hereafter, DDPS having a mutation that eliminates the feedback inhibition by L-lysine may also be referred to as "mutant DDPS", and a DNA encoding the mutant DDPS may also be referred to as "mutant dapA, or dapA*". AKIII derived from *E. coli* having a mutation that eliminates the feedback inhibition by L-lysine may also be referred to as "mutant AKIII", and a DNA encoding the mutant AKIII may also be referred to as "mutant lysC".

In the present invention, DDPS and AK are not necessarily required to be a mutant. It has been known that, for example, DDPS derived from *Corynebacterium* bacteria originally does not suffer feedback inhibition by L-lysine.

The plasmid used for gene cloning may be any plasmid so long as it can replicate in microorganisms such as Escherichia bacteria, and there can be specifically mentioned pBR322, pTWV228, pMW119, pUC19 and so forth.

The vector that functions in *Methylophilus* bacteria is, for example, a plasmid that can autonomously replicate in *Methylophilus* bacteria. Specifically, there can be mentioned RSF1010, which is a broad host spectrum vector, and derivatives thereof, for example, pAYC32 (Chistorerdov, A. Y., Tsygankov, Y. D. Plasmid, 16, 161–167 (1986)), pMFY42 (Gene, 44, 53 (1990)), pRP301, pTB70 (Nature, 287, 396, (1980)) and so forth.

In order to prepare a recombinant DNA by ligating dapA and lysC to a vector that functions in a *Methylophilus* bacteria, the vector is digested with a restriction enzyme that corresponds to the terminus of a DNA fragment containing dapA and lysC. Ligation is usually preformed by using ligase such as T4 DNA ligase. dapA and lysC may be individually incorporated into separate vectors or into the same vector.

As a plasmid containing a mutant dapA encoding a mutant DDPS and mutant lysC encoding a mutant AKIII, a broad host spectrum plasmid RSFD80 is known (WO95/16042). *E. coli* JM109 strain transformed with this plasmid was designated as AJ12396, and the strain was deposited at the National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary) on Oct. 28, 1993 and received an accession number of FERM P-13936. Then, it was converted to an international deposition under the provisions of the Budapest Treaty on Nov. 1, 1994, and received an accession number of FERM BP-4859. RSFD80 can be obtained from the AJ12396 strain by a known method.

In order to introduce a recombinant DNA prepared as described above into a *Methylophilus* bacterium, any method can be used so long as it provides sufficient transformation efficiency. For example, electroporation can be used (Canadian Journal of Microbiology, 43, 197 (1997)).

The DDPS activity and AK activity can also be enhanced by the presence of multiple copies of dapA and lysC on chromosomal DNA of a *Methylophilus* bacterium. In order to introduce multiple copies of dapA and lysC into chromosomal DNA of a *Methylophilus* bacterium, homologous recombination is performed by using a sequence that is present on chromosomal DNA in a as disclosed in Japanese Patent Laid-open No. 2-109985, multiple copies of dapA and/or lysc can be introduced into-chromosomal DNA by incorporating them into a transposon and transferring it. In both of the methods, as a result of increased copy numbers of dapA and lysC in transformant strains, activities of DDPS and AK should be amplified.

Besides the above gene amplification, the DDPS activity and AK activity can be amplified by replacing an expression control sequence such as promoters of dapA and lysC with stronger ones (refer to Japanese Patent Laid-open No. 1-215280). As such strong promoters, there are known, for example, lac promoter, trp promoter, trc promoter, tac promoter, $P_R$ promoter and $P_L$ promoter of lambda phage, tet promoter, amyE promoter, spac promoter and so forth. Substitution of these promoters enhances expression of dapA and lysC, and thus DDPS activity and AK activity are amplified. Enhancement of expression control sequences can be combined with increase of the copy numbers of dapA and lysC.

In order to prepare a recombinant DNA by ligating a gene fragment and a vector, the vector is digested with a restriction enzyme corresponding to the terminus of the gene fragment. Ligation is usually performed by ligase such as T4 DNA ligase. As methods for digestion, ligation and others of DNA, preparation of chromosomal DNA, PCR, preparation of plasmid DNA, transformation, design of oligonucleotides used as primers and so forth, usual methods well known to those skilled in the art can be used. Such methods are described in Sambrook, J., Fritsch, E. F., and Maniatis, T., "Molecular Cloning A Laboratory Manual, Second Edition", Cold Spring Harbor Laboratory Press (1989) and so forth.

In addition to the enhancement of DDPS and AK, other enzymes involved in the L-lysine biosynthesis may also be enhanced. Such enzymes include diaminopimelate pathway enzymes such as dihydrodipicolinate reductase, diaminopimelate decarboxylase, diaminopimelate dehydrogenase (refer to WO96/40934 for all of the foregoing enzymes), phosphoenolpyruvate carboxylase (Japanese Patent Laid-open No. 60-87788), aspartate aminotransferase (Japanese Patent Publication No. 6-102028), diaminopimelate epimerase and aspartic acid semialdehyde dehydrogenase, aminoadipate pathway enzymes such as homoaconitate hydratase and so forth.

Aspartokinase, aspartic acid semialdehyde dehydrogenase, dihydrodipicolinate synthase, dihydrodipicolinate reductase and diaminopimelate decarboxylase derived from *Methylophilus methylotrophus* will be explained later.

Further, the microorganisms of the present invention may have decreased activity of an enzyme that catalyzes a reaction for generating a compound other than L-lysine by branching off from the biosynthetic pathway for L-lysine, or may be deficient in such an enzyme. Illustrative examples of the enzyme that catalyzes a reaction for generating a compound other than L-lysine by branching off from the biosynthetic pathway for L-lysine include homoserine dehydrogenase (see WO95/23864).

The aforementioned techniques for enhancing activities of enzymes involved in the L-lysine biosynthesis can be similarly used for L-arginine.

L-Arginine producing ability can be improved by enhancing acetylornithine deacetylase activity, N-acetylglutamic acid-γ-semialdehyde dehydrogenase activity, N-acetyl glutamokinase activity and argininosuccinase activity (Japanese Patent Publication No. 5-23750).

L-Arginine producing ability can also be improved by enhancing activity of glutamate dehydrogenase (EP 1 057 893 A1), argininosuccinate synthase (EPO 999 267 A1), carbamoyl phosphate synthetase (EP1 026 247 A1) or N-acetylglutamate synthase (refer to Japanese Patent Laid-open No. 57-5693) or by disrupting the gene encoding an arginine repressor (argR).

<3> Production of L-lysine or L-arginine

L-Lysine or L-arginine can be produced by culturing a *Methylophilus* bacterium having L-lysine or L-arginine producing ability obtained as described above in a medium to produce and accumulate L-lysine or L-arginine in culture, and collecting the L-lysine or L-arginine from the culture.

The microorganism used for the present invention can be cultured by a method usually used for culture of a methanol assimilating microorganism. The medium used for the present invention may be either a natural or synthetic medium so long as it contains a carbon source, nitrogen source, inorganic ions and other trace amount organic components as required.

If methanol is used as a main carbon source, L-lysine or L-arginine can be produced at a low cost. When methanol is used as a main carbon source, it is added to a medium in an amount of 0.001–30%. As the nitrogen source, ammonium sulfate or the like is used by adding it to the medium. Other than these, there are added small amounts of the trace amount components such as potassium phosphate, sodium phosphate, magnesium sulfate, ferrous sulfate, manganese sulfate and so forth.

The culture is performed under an aerobic condition with shaking, aeration by stirring or the like at a pH of 5–9 and a temperature of 20–45° C., and it is usually terminated within 24–120 hours.

Collection of L-lysine or L-arginine from culture can be usually attained by a combination of known methods such as those using ion exchange resin, precipitation and others.

BEST MODE FOR CARRYING OUT THE INVENTION

Hereafter, the present invention will be explained more specifically with reference to the following examples. The reagents used in the following examples were obtained from Wako Pure Chemicals or Nakarai Tesque unless otherwise indicated. The compositions of the media used in each example are shown below. pH was adjusted with NaOH or HCl for all of the media.

(LB medium)

| | |
|---|---|
| Trypton peptone (Difco) | 10 g/L |
| Yeast extract (Difco) | 5 g/L |
| NaCl | 10 g/L |
| pH 7.0 | |

[These were steam-sterilized at 120° C. for 20 minutes.]
(LB agar medium)
LB medium

| | |
|---|---|
| Bacto agar | 15 g/L |

[These were steam-sterilized at 120° C. for 20 minutes.]
(SEII medium)

| | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 mg/L |
| $MnSO_4 \cdot 5H_2O$ | 25 mg/L |
| $ZnSO_4 \cdot 7H_2O$ | 23 mg/L |
| $CaCl_2 \cdot 2H_2O$ | 0.72 mg/L |
| $FeCl_3 \cdot 6H_2O$ | 9.7 mg/L |
| $CaCO_3$ (Kanto Kagaku) | 30 g/L |
| Methanol | 2% (vol/vol) |
| pH 7.0 | |

[Except for methanol, the components were steam-sterilized at 121° C. for 15 minutes. After the components were sufficiently cooled, methanol was added.]
(SEII agar medium)

| | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |

-continued

| | |
|---|---|
| CuSO$_4$.5H$_2$O | 5 mg/L |
| MnSO$_4$.5H$_2$O | 25 mg/L |
| ZnSO$_4$.7H$_2$O | 23 mg/L |
| CaCl$_2$.2H$_2$O | 0.72 mg/L |
| FeCl$_3$.6H$_2$O | 9.7 mg/L |
| Methanol | 0.5% (vol/vol) |
| pH 7.0 | |
| Bacto agar (Difco) | 15 g/L |
| [Except for methanol, the components were steam-sterilized at 121° C. for 15 minutes. After the components were sufficiently cooled, methanol was added.] | |

EXAMPLE 1

<1> Introduction of lysE Gene Derived from *Brevibacterium* bacterium into *Methylophilus* bacterium An lysE gene, which was a homologous gene of the gene facilitating excretion of L-lysine known for *Corynebacterium* bacteria, was cloned from a *Brevibacterium* bacterium, and it was attempted to express it in a *Methylophilus* bacterium.

(1) Construction of pRSlysE

In order to introduce lysE into a *Methylophilus* bacterium, a known plasmid pRS (refer to International Patent Publication in Japanese (Kohyo) No. 3-501682) was used to construct a plasmid pRSlysE for expression of lysE. pRS is a plasmid having the vector segment of the pVIC40 plasmid (International Patent Publication WO90/04636, International Patent Publication in Japanese No. 3-501682) and obtained from pVIC40 by deleting a DNA region encoding the threonine operon contained in the plasmid. The plasmid pVIC40 is derived from a broad host spectrum vector plasmid pAYC32 (Chistorerdov, A. Y., Tsygankov, Y. D., Plasmid, 1986, 16, 161–167), which is a derivative of RSF1010.

First, a plasmid pRStac having the tac promoter was constructed from pRS according to the scheme shown in FIG. 1. The pRStac plasmid was constructed as follows. The pRS vector was digested with restriction enzymes EcoRI and PstI and added with a phenol/chloroform solution and mixed with it to terminate the reaction. After the reaction mixture was centrifuged, the upper layer was collected, and DNA's were collected by ethanol precipitation and separated on 0.8% agarose gel. A DNA fragment of 8 kilobase pairs (henceforth abbreviated as "kbp") was collected by using EASY TRAP Ver. 2 (DNA collection kit, Takara Shuzo). On the other hand, the tac promoter region was amplified by PCR using the pKK223-3plasmid (expression vector, Pharmacia) as a template and the primers shown in SEQ ID NOS: 1 and 2 (a cycle consisting of denaturation at 94° C. for 20 seconds, annealing at 55° C. for 30 seconds and extension reaction at 72° C. for 60 seconds was repeated for 30 cycles). Pyrobest DNA polymerase (Takara Shuzo) was used for PCR. The DNA fragment containing the amplified tac promoter was purified by using PCR prep (Promega) and then digested at the restriction enzyme sites preliminarily designed in the primers, i.e., at EcoRI and EcoT22I sites. Then, the reaction mixture was added with a phenol/chloroform solution and mixed with it to terminate the reaction. After the reaction mixture was centrifuged, the upper layer was collected and DNA's were collected by ethanol precipitation and separated on 0.8% agarose gel. A DNA fragment of about 0.15 kbp was collected by using EASY TRAP Ver. 2.

The digestion product of the pRS vector and the tac promoter region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain pRStac. A plasmid in which the transcription directions of the streptomycin resistance gene on the pRS vector and the tac promoter were identical to each other was selected as pRStac.

pRStac obtained as described above was digested with Sse8387I (Takara Shuzo) and SapI (New England Biolabs), added with a phenol/chloroform solution and mixed with it to terminate the reaction. After the reaction mixture was centrifuged, the upper layer was collected and DNA's were collected by ethanol precipitation and separated on 0.8% agarose gel to obtain a DNA fragment of about 9.0 kbp.

The lysE gene fragment was also amplified by PCR using chromosome extracted from the *Brevibacterium lactofermentum* 2256 strain (ATCC13869) as a template and the primers shown in SEQ ID NOS: 5 and 6 (denaturation at 94° C. for 20 seconds, annealing at 55° C. for 30 seconds and extension reaction at 72° C. for 90 seconds). Pyrobest DNA polymerase (Takara Shuzo) was used for PCR. At this time, in order that expression of the lysE gene should become possible in a *Methylophilus* bacterium, the primers were designed so that nucleotides of 9–15 bp from the translation initiation codon of the lysE gene should be replaced with a sequence that had been known to function in a *Methylophilus* bacterium (Wyborn, N. R., Mills, J., Williamis, S. G. and Jones, C. W., Eur. J. Biochem., 240, 314–322 (1996)). The obtained fragment was purified by using PCR prep (Promega) and then digested with Sse8387I and SapI. The reaction mixture was added with a phenol/chloroform solution and mixed with it to terminate the reaction. After the reaction mixture was centrifuged, the upper layer was collected and DNA's were collected by ethanol precipitation and further collected from 0.8% agarose gel.

The digestion product of the pRStac vector and the lysE gene region fragment prepared as described above were ligated by using DNA Ligation Kit Ver. 2 (Takara Shuz o). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain pRSlysE (FIG. 1). In pRSlysE, the lysE gene was positioned so that its transcription direction should be the same as that of the tac promoter.

(2) Introduction of pRSlysE into *Methylophilus* Bacterium pRSlysE obtained as described above was introduced into *Methylophilus methylotrophus* AS1 strain (NCIMB10515) by electroporation (Canadian Journal of Microbiology, 43, 197 (1997)). In addition, pRS was also introduced into the ASI strain as a control in the same manner as that for pRSlysE. As a result, several thousands of colonies were obtained per 1 μg of DNA with pRS used as a control, whereas only several colonies were obtained with pRSlysE.

When plasmids were extracted from transformant strains estimated to be introduced with pRSlysE and their nucleotide sequences were investigated, a spontaneous mutation was introduced in a region encoding lysE for all the investigated plasmids, and in some cases, a nonsense mutation was introduced as the mutation, by which a codon encoding an amino acid was replaced with a stop codon that terminated the translation In other plasmids, deletion was observed in the lysE gene. It was considered that, in either case, the function of lysE carried by such plasmids should be lost. Further, when a plasmid in which a part of the region encoding lysE was intentionally deleted in such a manner that the function of the lysE gene should be eliminated (pRSlysEΔ1) was prepared and it was attempted to introduce it into *Methylophilus methylotrophus,* it could be introduced at a frequency equivalent to that of the pRS vector used as a control.

The aforementioned pRSlysEΔ1 was a plasmid in which a region from PvuI (recognizes CGATCG of the 203–209th positions in SEQ ID NO: 7) site to MluI (recognizes ACGCGT of the 485–491st positions of the same) site present in the region encoding lysE was deleted, and it was constructed as follows. Specifically, pRSlysE was digested with PvuI and MluI (Takara Shuzo), added with a phenol/chloroform solution and mixed with it to terminate the reaction. After the reaction mixture was centrifuged, the upper layer was collected and DNA's were collected by ethanol precipitation and separated on 0.8% agarose gel to obtain a DAN fragment of about 10 kbp. This DNA fragment was blunt-ended by using DNA Blunting Kit (Takara Shuzo). The product was ligated by itself (self-ligation) by using DNA Ligation Kit Ver. 2 (Takara Shuzo).

This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain the pRSlysEΔ1 plasmid.

As described above, the introduction frequency of pRSlysE carrying the full length lysE gene into *Methylophilus methylotrophus* was extremely low, and only plasmids having an lysE mutant gene introduced with a mutation that eliminated the function could be introduced. Considering these facts in combination, it was estimated that the introduction of the lysE gene into *Methylophilus methylotrophus* provided lethal effect. This indicates that the lysE gene cannot universally function as for the excretion of L-lysine in heterogenous bacteria.

The *Methylophilus methylotrophus* AS1 strain harboring pRSlysE introduced with a mutation was applied to an SEII plate containing 20 mg/L of streptomycin and cultured overnight at 37° C. Then, the cells of about 0.3 cm² of the medium surface were scraped, inoculated into SEII production medium (20 ml) containing 20 mg/L of streptomycin, and cultured at 37° C. for 34 hours with shaking. After completion of the culture, the cells were removed by centrifugation and the L-lysine concentration in the culture supernatant was determined by using an amino acid analyzer (Nihon Bunko, high speed liquid chromatography). As a result, substantially no strain was obtained in which excretion of L-lysine was enhanced in spite of introduction of the mutant lysE gene.

<2> Acquisition of Gene Providing L-lysine Excretion Activity in *Methylophilus* Bacteria As described in the preceding section, it was suggested that the known lysE gene should provide a lethal effect in *Methylophilus* bacteria, and many mutant genes of which function was lost were obtained.

During analysis of pRSlysE introduced with a mutation, a mutant lysE gene that functioned in *Methylophilus* bacteria could be obtained.

This mutant lysE gene was designated as lysE24 gene. When the nucleotide sequence of lysE24 gene was analyzed, it was found that this mutation was not a mutation causing amino acid substitution, but a nonsense mutation introducing a stop codon around the center of the translation region of lysE. It has been reported that the lysE gene of *Corynebacterium* bacteria encodes a membrane protein having six hydrophobic helixes (Vrlijc M., Sahm H., and Eggeling L., Molecular Microbiology 22:815–826 (1996)). In contrast, it was found that, since the above lysE24 gene was introduced with a stop codon, the protein encoded by this gene had a structure different from that of the LysE protein encoded by a wild-type lysE gene, and it functioned in *Methylophilus* bacteria thanks to this structure.

The result of nucleotide sequence determination of lysE24 is shown in SEQ ID NO: 9. The nucleotide sequence of wild-type lysE is shown in SEQ ID NO: 7 as reference. In lysE24, T (thymine) was inserted after G (guanine) at the 355th position of SEQ ID NO: 7. The plasmid having this lysE24 was designated as pRSlysE24 (FIG. 1). When pRSlysE24 was introduced anew into the AS1 strain, the plasmid could be introduced at a frequency substantially equivalent to that of pRS. In Table 1, there is shown the result of L-lysine concentration measurement for culture supernatant of the plasmid-introduced strain, which measurement was performed in the same manner as in <1>, (2).

TABLE 1

| Strain | Production amount of L-lysine (g/L) |
|---|---|
| AS1/pRS | <0.01 |
| AS1/PRSlysE24 | 0.1 |

The *E. coli* JM109 strain transformed with pRSlysE24 was designated as AJ13830, and this strain was deposited at the independent administrative corporation, National Institute of Advanced Industrial Science and Technology, International Patent Organism Depositary on Jun. 4, 2001 and received an accession number of FERM P-18369. Then, it was converted to an international deposition under the provisions of the Budapest Treaty on May 13, 2002, 2002, and received an accession number of FERM BP-8040.

When the lysE24 gene of which region downstream from the stop codon produced by the aforementioned mutation was deleted was introduced into the AS1 strain, the strain did not accumulate L-lysine in the medium.

EXAMPLE 2

Introduction of L-lysine Biosynthesis System Enzyme Gene and lysE24 Gene into *Methylophilus methylotrophus*

It was found that, when the lysE24 gene was introduced into *Methylophilus methylotrophus* AS1 strain, L-lysine was accumulated in the medium. It was considered that this was caused by enhancement of the excretion of L-lysine.

The inventors of the present invention had clarified that, if an L-lysine biosynthesis gene had been enhanced by a plasmid in a *Methylophilus* bacterium, a marked amount of L-lysine had been accumulated in a medium (Japanese Patent Application No. 11-368097). Therefore, there was investigated an effect of introduction of the lysE24 gene into *Methylophilus methylotrophus* of which L-lysine biosynthesis gene was enhanced.

<1> Construction of Plasmid pRSdapA Having dapA* Gene

There was prepared a plasmid having a gene encoding dihydrodipicolinate synthase that did not suffer feedback inhibition by L-lysine (dapA*) as an L-lysine biosynthesis system enzyme gene.

pRStac prepared in Example 1 was digested with Sse8387I and XbaI and added with a phenol/chloroform solution and mixed with it to terminate the reaction. After the reaction mixture was centrifuged, the upper layer was collected, and DNA's were collected by ethanol precipitation and separated on 0.8% agarose gel to collect a DNA fragment of about 9 kbp.

The dapA* gene fragment was amplified by PCR using the known plasmid RSFD80 (refer to WO95/16042) containing that gene as a template and the primers shown in SEQ ID NOS: 3 and 4 (denaturation at 94° C. for 20 seconds, annealing at 55° C. for 30 seconds and extension reaction at 72° C. for 60 seconds). Pyrobest DNA polymerase (Takara Shuzo) was used for PCR. The obtained dapA* fragment was purified by using PCR prep (Promega) and then digested with restriction enzymes Sse8387I and XbaI. The reaction mixture was added with a phenol/chloroform solution and mixed with it to terminate the reaction. After the reaction mixture was centrifuged, the upper layer was collected and DNA's were collected by ethanol precipitation and separated on 0.8% agarose gel to collect a DAN fragment of about 0.1 kbp.

The digestion product of the pRStac vector and the dapA* gene region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain a pRSdapA plasmid. In pRSdapA plasmid, the dapA* gene was positioned so that its transcription direction should be the same as that of the tac promoter.

<2> Introduction of pRSlysE24 or pRSdapA into *Methylophilus methylotrophus* AS1 Strain pRSdapA obtained as described above was introduced into *Methylophilus methylotrophus* ASI strain by electroporation. As for the obtained transformant (henceforth also referred to as "AS1/pRSdapA"), the aforementioned *Methylophilus methylotrophus* AS1 strain introduced with pRSlysE24 (henceforth also referred to as "AS1/pRSlysE24") and the *Methylophilus methylotrophus* AS1 strain introduced with the pRS plasmid (henceforth also referred to as "AS1/pRS") as a control, the intracellular L-amino acid concentration and the L-amino acid concentration in culture supernatant were determined.

Each transformant strain was cultured overnight at 37° C. on an SEII plate containing 20 mg/L of streptomycin. Then, the cells of about 0.3 cm$^2$ of the medium surface were scraped, inoculated into SEII production medium (20 ml) containing 20 mg/L of streptomycin, and cultured at 37° C. for 24 hours with shaking. After completion of the culture, the cells were removed from a part of the culture broth by centrifugation and the L-amino acid concentration in the culture supernatant was determined by using an amino acid analyzer. The remaining culture broth was passed through silicone oil to separate the culture broth and the cells according to the method of Kinnbier et al. (Dinnbier et al., Arch. Microbiol 150:348–357 (1988)). Amino acids in the cells were extracted with perchloric acid, and the L-amino acid concentration was measured by using an amino acid analyzer. At this time, concentration of proteins contained in the cells was simultaneously measured, and the intracellular L-lysine concentration was represented as an amount per unit weight of the intracellular proteins.

The results are shown in Table 2. With AS1/pRSlysE24, L-lysine accumulation substantially equivalent to that of AS1/pRSdapA was observed in the medium. On the other hand, with AS1/pRSlysE24, the intracellular L-lysine concentration was suppressed to a low level, and it was considered that L-lysine was excreted to outside of the cells due to the introduction of the lysE24 gene.

TABLE 2

| strain | L-lysine concentration in culture supernatant (g/L) | intracellular L-lysine concentration (g/mg-protein) |
|---|---|---|
| AS1/pRS | <0.01 | 1.60 |
| AS1/PRSlysE24 | 0.10 | 2.80 |
| AS1/PRSdapA | 0.12 | 17.3 |

Further, concentrations of other L-amino acids in the culture supernatant were also investigated. As a result, it was found that L-arginine accumulated in AS1/pRSlysE24. Thus, it was found that lysE24 had excretion activity not only for L-lysine but also for L-arginine. The results are shown in Table 3.

TABLE 3

| Strain | L-Arginine concentration in culture supernatant (g/L) |
|---|---|
| AS1/pRS | <0.01 |
| AS1/PRSlysE24 | 0.04 |

The *E. coli* JM109 strain transformed with the pRSdapA plasmid was designated as AJ13831, and this strain was deposited at the independent administrative corporation, National Institute of Advanced Industrial Science and Technology, International Patent Organism Depositary on Jun. 4, 2001 and received an accession number of FERM P-18370. Then, it was converted to an international deposition under the provisions of the Budapest Treaty on May 13, 2002, and received an accession number of FERM BP-8041.

<3> Introduction of lysE24 Gene and dapA* Gene into *Methylophilus methylotrophus* AS1 Strain It was found that, although the excretion of L-lysine to the outside of cells constituted a rate-limiting factor in the L-lysine production by *Methylophilus methylotrophus* AS1 strain, the excretion of L-lysine to the outside of cells was enhanced by the introduction of the lysE24 gene. Therefore, it was attempted to further improve the productivity by enhancing the L-lysine biosynthesis enzyme system in a strain introduced with the lysE24 gene.

(1) Construction of Plasmid Having lysE24 and dapA*

Figure 2:
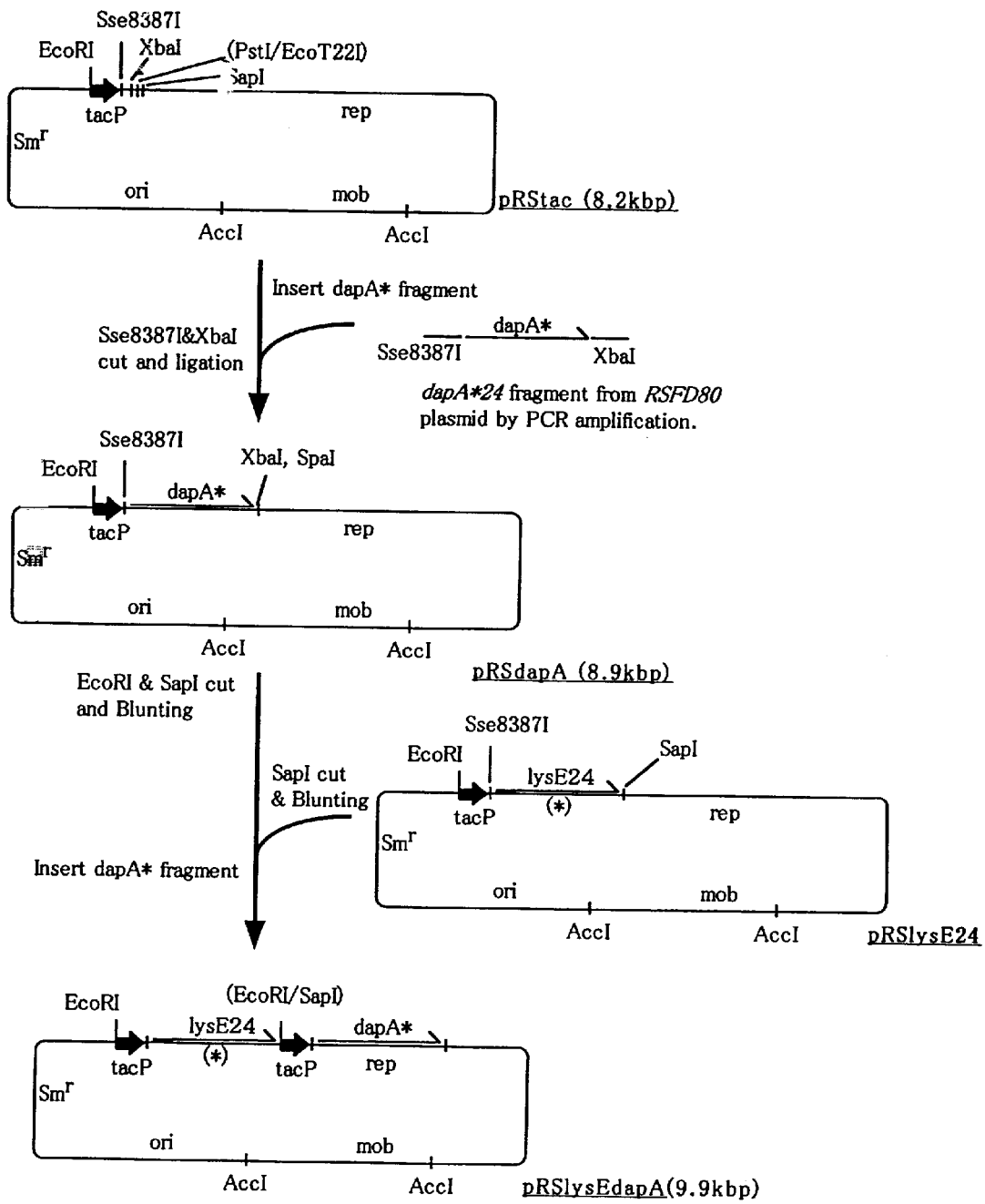
FIG. 2 shows construction of a plasmid pRSlysEdapA having the lysE24 gene and dapA* gene.

In order to evaluate effect of combination of lysE24 and dapA*, a plasmid consisting of the pRSlysE plasmid inserted with the dapA* gene was constructed in the scheme shown in FIG. 2. pRSlysE24 prepared in Example 1 was digested with a restriction enzyme SapI and ends of the product were blunt-ended by using DNA Blunting Kit (Takara Shuzo). Further, the plasmid pRSdapA having dapA* was digested with restriction enzymes EcoRI and SapI, and a fragment of about 1 kbp containing the tac promoter and the dapA* region was separated on 0.8% agarose gel and collected by using EASY TRAP Ver 2 (Takara Shuzo). This fragment was blunt-ended in the same manner as described above and ligated to the aforementioned digestion product of pRSlysE24 by using DNA Ligation Kit Ver 2 (Takara Shuzo).

This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain a pRSlysEdapA plasmid. In this plasmid, the lysE24 gene and the dapA* gene were positioned so that their transcription directions should be identical to each other.

pRSlysEdapA obtained as described above as well as pRSlysE24, pRSdapA and pRS plasmids as controls were each introduced into *Methylophilus methylotrophus* AS1 strain (NCIMB10515) by electroporation.

(2) Production of L-lysine by *Methylophilus* Bacterium Harboring lysE24 and dapA*

Each of the AS1 strains introduced with pRSlysEdapA, pRSlysE24, pRSdapA or pRS, which were obtained as described above, was applied to an SEII plate containing 20 mg/L of streptomycin and cultured overnight at 37° C. Then, the cells of about 0.3 cm$^2$ of the medium surface were scraped, inoculated into SEII production medium (20 ml) containing 20 mg/L of streptomycin, and cultured at 37° C. for 34 hours with shaking. After completion of the culture, the cells were removed by centrifugation and the L-lysine concentration in the culture supernatant was determined by using an amino acid analyzer (Nihon Bunko, high speed liquid chromatography). The results are shown in Table 4. The strain introduced with pRSlysEdapA showed L-lysine accumulation in the medium about 10 times higher than that shown by the strain introduced only with pRSdapA or pRSlysE24. Thus, it can be seen that the rate-limiting effect by the excretion was canceled by the introduction of the lysE24 gene and the effect of the enhancement of the dapA* gene was synergistically manifested.

TABLE 4

| Strain | L-Lysine production amount (g/L) |
| --- | --- |
| AS1/pRS | <0.01 |
| AS1/pRSlysE24 | 0.10 |
| AS1/pRSdapA | 0.12 |
| AS1/pRSlysEdapA | 1.20 |

The *E. coli* JM109 strain transformed with the pRSlysEdapA plasmid was designated as AJ13832, and this strain was deposited at the independent administrative corporation, National Institute of Advanced Industrial Science and Technology, International Patent Organism Depositary on Jun. 4, 2001 and received an accession number of FERM P-18371. Then, it was converted to an international deposition under the provisions of the Budapest Treaty on May 13, 2002, 2002, and received an accession number of FERM BP-8042.

What is claimed is:

1. A plasmid containing a DNA sequence, wherein said sequence comprises SEQ ID NO: 7, but does not have the ioop region of nucleotides 280–435.

2. The plasmid of claim 1, wherein said sequence is SEQ ID NO: 9.

3. The plasmid of claim 1, wherein said DNA encodes a protein having the amino acid sequence of SEQ ID NO: 10.

4. An isolated recombinant cell containing a DNA sequence which encodes a protein having the amino acid sequence of SEQ ID NO: 10, wherein said DNA sequence has been integrated into the chromosome of the cell.

5. A recombinant cell which has been transformed with the plasmid of claim 1.

6. A recombinant cell which has been transformed with the plasmid of claim 2.

7. A recombinant cell which has been transformed with the plasmid of claim 3.

8. The cell of claim 4, wherein the cell is *Methylophilus*.

9. The cell of claim 5, wherein the cell is *Methylophilus*.

10. The cell of claim 6, wherein the cell is *Methylophilus*.

11. The cell of claim 7, wherein the cell is *Methylophilus*.

12. A method of producing L-lysine or L-arginine comprising culturing the recombinant cell according to claim 4 in a medium, allowing L-lysine or L-arginine to be secreted out of said cell into said medium, and collecting the L-lysine or L-arginine.

13. A method of producing L-lysine or L-arginine comprising culturing the recombinant cell according to claim 5 in a medium, allowing L-lysine or L-arginine to be secreted out of said cell into said medium, and collecting the L-lysine or L-arginine.

14. A method of producing L-lysine or L-arginine comprising culturing the recombinant cell according to claim 6 in a medium, allowing L-lysine or L-arginine to be secreted out of said cell into said medium, and collecting the L-lysine or L-argnine.

15. A method of producing L-lysine or L-arginine comprising culturing the recombinant cell according to claim 7 in a medium, allowing L-lysine or L-arginine to be secreted out of said cell into said medium, and collecting the L-lysine or L-arginine.

16. The method of claim 12, wherein the cell is *Methylophilus*.

17. The method of claim 13, wherein the cell is *Methylophilus*.

18. The method of claim 14, wherein the cell is *Methylophilus*.

19. The method of claim 15, wherein the cell is *Methylophilus*.

* * * * *

UNITED STATES PATENT AND TRADEMARK OFFICE
CERTIFICATE OF CORRECTION

PATENT NO.       : 7,169,587 B2                                               Page 1 of 1
APPLICATION NO.  : 10/166142
DATED            : January 30, 2007
INVENTOR(S)      : Gunji et al.

It is certified that error appears in the above-identified patent and that said Letters Patent is hereby corrected as shown below:

Col. 25, delete Claim 1, and replace with the following:

1. A plasmid containing a DNA sequence, wherein said sequence comprises SEQ ID NO: 7, but does not have the loop region of nucleotides 280-435.

Signed and Sealed this

First Day of May, 2007

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 39
<212> TYPE: DNA
<213> ORGANISM: Artificial Sequence
<220> FEATURE:
<223> OTHER INFORMATION: synthetic DNA

<400> SEQUENCE: 1
agggaattcc ccgttctgga taatgttttt tgcgccgac                          39

<210> SEQ ID NO 2
<211> LENGTH: 58
<212> TYPE: DNA
<213> ORGANISM: Artificial Sequence
<220> FEATURE:
```

```
<223> OTHER INFORMATION: synthetic DNA

<400> SEQUENCE: 2
cggatgcatc tagagttaac ctgcagggtg aaattgttat ccgctcacaa ttccacac         58

<210> SEQ ID NO 3
<211> LENGTH: 35
<212> TYPE: DNA
<213> ORGANISM: Artificial Sequence
<220> FEATURE:
<223> OTHER INFORMATION: synthetic DNA

<400> SEQUENCE: 3
tgacctgcag gtttgcacag aggatggccc atgtt                                  35

<210> SEQ ID NO 4
<211> LENGTH: 36
<212> TYPE: DNA
<213> ORGANISM: Artificial Sequence
<220> FEATURE:
<223> OTHER INFORMATION: synthetic DNA

<400> SEQUENCE: 4
cattctagat ccctaaactt tacagcaaac cggcat                                 36

<210> SEQ ID NO 5
<211> LENGTH: 64
<212> TYPE: DNA
<213> ORGANISM: Artificial Sequence
<220> FEATURE:
<223> OTHER INFORMATION: synthetic DNA

<400> SEQUENCE: 5
catttcctgc aggcaaagga gatgagcgta atggtgatca tggaaatctt cattacaggt       60
ctgc                                                                    64

<210> SEQ ID NO 6
<211> LENGTH: 50
<212> TYPE: DNA
<213> ORGANISM: Artificial Sequence
<220> FEATURE:
<223> OTHER INFORMATION: synthetic DNA

<400> SEQUENCE: 6
gggcgagcta aaagagctcc aaaacccgcg aaaactaacc catcaacatc                  50

<210> SEQ ID NO 7
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)
<223> OTHER INFORMATION:

<400> SEQUENCE: 7 atg gtg atc atg gaa atc ttc att aca ggt ctg ctt ttg ggg gcc agt         48
Met Val Ile Met Glu Ile Phe Ile Thr Gly Leu Leu Leu Gly Ala Ser
1               5                   10                  15 ctt tta ctg tcc atc gga ccg cag aat gta ctg gtg att aaa caa gga         96
Leu Leu Leu Ser Ile Gly Pro Gln Asn Val Leu Val Ile Lys Gln Gly
            20                  25                  30 att aag cgc gaa gga ctc att gcg gtt ctt ctc gtg tgt tta att tct        144
Ile Lys Arg Glu Gly Leu Ile Ala Val Leu Leu Val Cys Leu Ile Ser
        35                  40                  45
```

```
gac gtc ttt ttg ttc atc gcc ggc acc ttg ggc gtt gat ctt ttg tcc        192
Asp Val Phe Leu Phe Ile Ala Gly Thr Leu Gly Val Asp Leu Leu Ser
 50                  55                  60 aat gcc gcg ccg atc gtg ctc gat att atg cgc tgg ggt ggc atc gct        240
Asn Ala Ala Pro Ile Val Leu Asp Ile Met Arg Trp Gly Gly Ile Ala
 65                  70                  75                  80 tac ctg tta tgg ttt gcc gtc atg gca gcg aaa gac gcc atg aca aac        288
Tyr Leu Leu Trp Phe Ala Val Met Ala Ala Lys Asp Ala Met Thr Asn
                 85                  90                  95 aag gtg gaa gcg cca cag atc att gaa gaa aca gaa cca acc gtg ccc        336
Lys Val Glu Ala Pro Gln Ile Ile Glu Glu Thr Glu Pro Thr Val Pro
                100                 105                 110 gat gac acg cct ttg ggc ggt tcg gcg gtg gcc act gac acg cgc aac        384
Asp Asp Thr Pro Leu Gly Gly Ser Ala Val Ala Thr Asp Thr Arg Asn
            115                 120                 125 cgg gtg cgg gtg gag gtg agc gtc gat aag cag cgg gtt tgg gta aag        432
Arg Val Arg Val Glu Val Ser Val Asp Lys Gln Arg Val Trp Val Lys
130                 135                 140 ccc atg ttg atg gca atc gtg ctg acc tgg ttg aac ccg aat gcg tat        480
Pro Met Leu Met Ala Ile Val Leu Thr Trp Leu Asn Pro Asn Ala Tyr
145                 150                 155                 160 ttg gac gcg ttt gtg ttt atc ggc ggc gtc ggc gcg caa tac ggc gac        528
Leu Asp Ala Phe Val Phe Ile Gly Gly Val Gly Ala Gln Tyr Gly Asp
                165                 170                 175 acc gga cgg tgg att ttc gcc gct ggc gcg ttc gcg gca agc ctg atc        576
Thr Gly Arg Trp Ile Phe Ala Ala Gly Ala Phe Ala Ala Ser Leu Ile
            180                 185                 190 tgg ttc ccg ctg gtg ggt ttc ggc gca gca gca ttg tca cgc ccg ctg        624
Trp Phe Pro Leu Val Gly Phe Gly Ala Ala Ala Leu Ser Arg Pro Leu
        195                 200                 205 tcc agc ccc aag gtg tgg cgc tgg atc aac gtc gtc gtg gca gtt gtg        672
Ser Ser Pro Lys Val Trp Arg Trp Ile Asn Val Val Val Ala Val Val
210                 215                 220 atg acc gca ttg gcc atc aaa ctg atg ttg atg ggt tag                    711
Met Thr Ala Leu Ala Ile Lys Leu Met Leu Met Gly
225                 230                 235

<210> SEQ ID NO 8
<211> LENGTH: 236
<212> TYPE: PRT
<213> ORGANISM: Brevibacterium lactofermentum

<400> SEQUENCE: 8

Met Val Ile Met Glu Ile Phe Ile Thr Gly Leu Leu Leu Gly Ala Ser
 1               5                  10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
 50                  55                  60

Asn Ala Ala Pro Ile Val Leu Asp Ile Met Arg Trp Gly Gly Ile Ala
 65                  70                  75                  80

Tyr Leu Leu Trp Phe Ala Val Met Ala Ala Lys Asp Ala Met Thr Asn
                 85                  90                  95

Lys Val Glu Ala Pro Gln Ile Ile Glu Glu Thr Glu Pro Thr Val Pro
                100                 105                 110

Asp Asp Thr Pro Leu Gly Gly Ser Ala Val Ala Thr Asp Thr Arg Asn
```

```
                115                 120                 125
Arg Val Arg Val Glu Val Ser Val Asp Lys Gln Arg Val Trp Val Lys
        130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Val Gly Ala Gln Tyr Gly Asp
                165                 170                 175

Thr Gly Arg Trp Ile Phe Ala Ala Gly Ala Phe Ala Ala Ser Leu Ile
                180                 185                 190

Trp Phe Pro Leu Val Gly Phe Gly Ala Ala Ala Leu Ser Arg Pro Leu
        195                 200                 205

Ser Ser Pro Lys Val Trp Arg Trp Ile Asn Val Val Ala Val Val
        210                 215                 220

Met Thr Ala Leu Ala Ile Lys Leu Met Leu Met Gly
225                 230                 235

<210> SEQ ID NO 9
<211> LENGTH: 712
<212> TYPE: DNA
<213> ORGANISM: Brevibacterium lactofermentum
<220> FEATURE:
<221> NAME/KEY: CDS
<222> LOCATION: (1)..(375)
<223> OTHER INFORMATION:

<400> SEQUENCE: 9 atg gtg atc atg gaa atc ttc att aca ggt ctg ctt ttg ggg gcc agt    48
Met Val Ile Met Glu Ile Phe Ile Thr Gly Leu Leu Leu Gly Ala Ser
1               5                   10                  15 ctt ttg ctg tcc atc gga ccg cag aat gta ctg gtg att aaa caa gga    96
Leu Leu Leu Ser Ile Gly Pro Gln Asn Val Leu Val Ile Lys Gln Gly
                20                  25                  30 att aag cgc gaa gga ctc att gcg gtt ctt ctc gtg tgt tta att tct   144
Ile Lys Arg Glu Gly Leu Ile Ala Val Leu Leu Val Cys Leu Ile Ser
            35                  40                  45 gac gtc ttt ttg ttc atc gcc ggc acc ttg ggc gtt gat ctt ttg tcc   192
Asp Val Phe Leu Phe Ile Ala Gly Thr Leu Gly Val Asp Leu Leu Ser
        50                  55                  60 aat gcc gcg ccg atc gtg ctc gat att atg cgc tgg ggt ggc atc gct   240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac   288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc   336
Lys Val Glu Ala Pro Gln Ile Ile Glu Glu Thr Glu Pro Thr Val Pro
                100                 105                 110 gat gac acg cct ttg ggc gtg ttc ggc ggt ggc cac tga cacgcgcaac   385
Asp Asp Thr Pro Leu Gly Val Phe Gly Gly Gly His
            115                 120 cgggtgcggg tggaggtgag cgtcgataag cagcgggttt gggtgaagcc catgttgatg   445
gcaatcgtgc tgacctggtt gaacccgaat gcgtatttgg acgcgtttgt gtttatcggc   505
ggcgtcggcg cgcaatacgg cgacaccgga cggtggattt cgccgctgg cgcgttcgcg   565 gcaagcctga tctggttccc gctggtgggt tcggcgcag cagcattgtc acgcccgctg   625
tccagcccca aggtgtggcg ctggatcaac gtcgtcgtgg cagttgtgat gaccgcattg   685
gccatcaaac tgatgttgat gggttag                                      712
```

```
<210> SEQ ID NO 10
<211> LENGTH: 124
<212> TYPE: PRT
<213> ORGANISM: Brevibacterium lactofermentum

<400> SEQUENCE: 10

Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
                20                  25                  30

Ile Lys Arg Glu Gly Leu Ile Ala Val Leu Leu Val Cys Leu Ile Ser
            35                  40                  45

Asp Val Phe Leu Phe Ile Ala Gly Thr Leu Gly Val Asp Leu Leu Ser
        50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Val Phe Gly Gly Gly His
            115                 120
```